United States Patent [19]

Fergason et al.

[11] Patent Number: 5,252,817
[45] Date of Patent: Oct. 12, 1993

[54] DETECTOR SYSTEM FOR DETECTING THE OCCURRENCE OF WELDING USING DETECTOR FEEDBACK

[75] Inventors: John D. Fergason, Sunnyvale; Jeffrey K. Fergason, Menlo Park, both of Calif.

[73] Assignee: OSD Envizion Company, Menlo Park, Calif.

[21] Appl. No.: 674,850

[22] Filed: Mar. 25, 1991

[51] Int. Cl.$^5$ ............................................. G01J 1/32
[52] U.S. Cl. .................................. 250/205; 250/214 B; 250/214 RC
[58] Field of Search ............ 250/205, 214 RC, 214 B, 250/214 R; 307/359, 494

[56] References Cited

U.S. PATENT DOCUMENTS

| | | |
|---|---|---|
| Re. 29,684 | 6/1978 | Gordon . |
| Re. 32,521 | 10/1987 | Fergason . |
| 2,423,320 | 7/1947 | Hurley . |
| 2,761,046 | 8/1956 | Herrick et al. . |
| 3,137,784 | 6/1964 | Kasemann . |
| 3,245,315 | 4/1966 | Marks et al. . |
| 3,575,491 | 4/1971 | Heilmeier . |
| 3,731,986 | 5/1973 | Fergason . |
| 3,873,804 | 3/1975 | Gordon . |
| 3,881,808 | 5/1975 | Gurtler et al. . |
| 3,890,628 | 6/1975 | Gurtler . |
| 3,918,796 | 11/1975 | Fergason . |
| 3,967,881 | 6/1976 | Katano et al. . |
| 4,039,254 | 8/1977 | Harsch . |
| 4,071,912 | 2/1978 | Budmiger . |
| 4,109,114 | 8/1978 | Baer et al. .................. 250/214 B |
| 4,240,709 | 12/1980 | Hornell . |
| 4,279,474 | 7/1981 | Belgorod . |
| 4,385,806 | 5/1983 | Fergason . |
| 4,436,376 | 3/1984 | Fergason . |
| 4,540,243 | 9/1985 | Fergason . |
| 4,556,289 | 12/1985 | Fergason . |
| 4,560,239 | 12/1985 | Katz . |
| 4,728,173 | 5/1988 | Toth . |
| 4,821,292 | 4/1989 | Childress ..................... 307/359 |
| 4,863,244 | 9/1989 | Fuerthbauer et al. . |

FOREIGN PATENT DOCUMENTS

| | | |
|---|---|---|
| 0157744 | 9/1985 | European Pat. Off. . |
| 0335056 | 4/1989 | European Pat. Off. . |
| 0349665 | 10/1990 | European Pat. Off. . |
| 2315308 | 10/1973 | Fed. Rep. of Germany . |
| 2530039A | 1/1984 | France . |
| 55-92276 | 7/1980 | Japan . |
| 59-111102 | 6/1984 | Japan . |
| 73127334 | 7/1977 | Sweden . |
| 7608690-9 | 2/1979 | Sweden . |
| 325586 | 2/1930 | United Kingdom . |
| 90/14809 | 12/1990 | World Int. Prop. O. . |

OTHER PUBLICATIONS

U.S. application Ser. No. 365,167, filed Jun. 6, 1989.
U.S. application Ser. No. 653,661, filed Feb. 1991.

Primary Examiner—David C. Nelms
Assistant Examiner—Que T. Le
Attorney, Agent, or Firm—Renner, Otto, Boisselle & Sklar

[57] ABSTRACT

A power supply circuit for a liquid crystal welding lens or shutter develops a relatively low voltage AC signal for driving or powering the liquid crystal shutter to the clear state and two relatively higher or larger magnitude AC electrical signals for initially driving the shutter to the dark state and then for maintaining the shutter in the dark state; a variable frequency circuit for varying the frequency of the driving signal to the shutter to minimize power usage in the dark state and to avoid flicker in the clear state; and power saving and battery level indicator features are included.

15 Claims, 4 Drawing Sheets

DETECTOR SYSTEM FOR DETECTING THE OCCURRENCE OF WELDING USING DETECTOR FEEDBACK

TECHNICAL FIELD

The present invention relates generally, as is indicated, to driving circuits for liquid crystal shutters and, more particularly, to a high speed driving circuit for a liquid crystal shutter operable to control transmission of light therethrough.

BACKGROUND

The present invention is described below with respect to a liquid crystal shutter. It will be appreciated, though, that features of the invention may be utilized with shutters formed of materials other than liquid crystal and also may be utilized with devices other than shutters. A shutter, as is used herein, refers to a device for controlling intensity of electromagnetic energy or electromagnetic radiation that is being transmitted through the shutter. In the preferred embodiment described in detail below, such electromagnetic energy is in the form of light and more preferably is in the form of light (i.e., electromagnetic energy) that is in the visible spectrum as well as in the various infrared spectra and ultraviolet spectra, all collectively referred to as light below. Such control may be by way of graduated or analog control or intensity of transmitted light preferably without detrimentally affecting the image characteristics of such light. Such control also may be digital, i.e., on, off, and specific intermediate levels of transmission or intensity, etc.

An exemplary liquid crystal shutter with which the driving circuit of the invention may be utilized is disclosed in U.S. Pat. Nos. 4,385,806, 4,436,376, 4,540,243, and Re. 32,521. An example of such shutter includes a pair of linear (plane) polarizers, one being used as an input polarizer and the other as an output analyzer, and a variable liquid crystal optical retarder between the two polarizers. By changing the electric field applied to liquid crystal in the retarder, the plane of polarization (or relationships of the axes of elliptically polarized light) of the light transmitted through the retarder can be changed; and the intensity of light transmitted through the analyzer will be a function of the polarization direction (characteristics) of the light transmitted through the retarder.

A shutter system which may employ such an exemplary liquid crystal shutter is disclosed in copending, commonly owned U.S. patent application Ser. No. 07/653,661 filed Feb. 8, 1991, for "Eye Protection System For Welding Helmets And The Like". The present invention is useful to provide electrical power and to operate such a shutter system.

The disclosures of such patents and patent application are incorporated in their entireties by this express reference thereto.

One approach to providing for high speed operation, for example, in the microsecond range, as compared to the millisecond range, say on the order of 500 microseconds or faster, and preferably in the range of from several microseconds to several tens of microseconds, for the optical shutters of such patents and patent applications, as well as other similar shutters, is according to surface mode effect, whereby that liquid crystal material located near the center of the liquid crystal cell along the optical transmission direction through the cell is maintained in a preferred alignment during cell operation in a clear state, whereas liquid crystal material nearer the respective surfaces of the cell, i.e., the interface between the liquid crystal material and the respective glass plates, is switched to switch between clear and dark states as a function of the applied electric field, as is described in detail in the above-mentioned patents and patent application. Due to birefringence characteristics of the liquid crystal material, for example, nematic liquid crystal, changes in the thickness of differently aligned liquid crystal layers varies retardation effect on transmitted polarized light. Absent adequate field voltage the liquid crystal near the surface aligns generally parallel or slightly tilted with respect to the surface, and such surface "layer(s)" of liquid crystal tend to align with the field when the field voltage is adequately large. In one embodiment some means, such as a bias voltage or electric field, a functionally equivalent rms driving method, or some other means or mechanism, is used to obtain the preferred alignment of liquid crystal material near the center of the cell. In an example, application of a larger voltage/electric field compared to the exemplary bias voltage/electric field, effects switching of the alignment of the liquid crystal material nearer the surfaces.

As is well known, the transition speed for a liquid crystal cell, whether of the twisted nematic type, dyed cell type or surface mode type, is asymmetrical; in particular, such a liquid crystal cell operates faster to achieve an operational condition, e.g., alignment of liquid crystal structure or directors, when driven to that condition by an electric field (or an increase in the field magnitude), than it operates when relaxing to a deenergized or reduced energization state, e.g., reduction or elimination of the electric field. Therefore, for maximum speed of operation to the dark state for eye protection, for example, it is desirable in a welding lens environment that the liquid crystal lens be operated with maximum power to achieve the darkest eye protection state. Also, a surface mode liquid crystal cell usually responds to energization significantly faster than twisted nematic liquid crystal cell, and it, therefore, provides for faster operation in accordance with the present invention.

The exemplary shutter may be used in a variety of embodiments and applications. One example is as a lens or shutter for a welding helmet. Therefore, the terms "lens" and "welding lens" are used synonymously with "shutter" and, as used herein means the device through which an image is viewed without necessarily having any focusing or optical refraction characteristics. The lens or shutter is adjustable to control light, i.e., to increase or to decrease the amount of the incident light which is transmitted through the shutter. When welding is not occurring, the shutter may be substantially optically clear to transmissive or at least minimizes its attenuation of light. When welding is occurring, the shutter may be dark or closed to minimize the amount of light transmitted therethrough in order to protect the eyes of the person performing the welding. In both cases, though, the image characteristics of the light remain intact. A photosensitive device may be used to sense the intensity of light impinging in the area of the shutter so as to provide an input to a drive circuit for the shutter in order to control opening and closing thereof. As is described in the above patent application, a third state or condition of the welding lens or shutter may exist, namely a deenergized state or condition. Such third state preferably is darker than the clear state.

The invention is especially useful for eye protection wherein high speed protective shuttering and protective fail state are desired. Exemplary uses are in welding helmets, spectacles, goggles, and the like, as well as safety goggles for nuclear flash protection, for protection from hazards experienced by electric utility workers and for workers at furnace and electric plant areas and at other places where bright light that could present a risk of injury may occur.

Shade number or shade is the characterization of darkness of a welding lens, for example, (hereinafter sometimes simply referred to as lens); a larger shade number represents a darker, more light blocking (or absorbing) or less optically transmissive lens and a smaller shade number represents a less dark, less light blocking (or absorbing) or more optically transmissive lens. Generally optical transmission means transmission of light and the image or view carried by the light without substantial distortion of the image, e.g., due to scattering. Shade number is a term of art often used in the field of welding and especially welding lenses for eye protection.

Clear state or clear shade means the state of highest operating luminous transmittance (or light transmission) of the lens. This state corresponds to the state having the lowest shade number for the lens.

Dark state or dark shade is the lowest operating luminous transmittance (or light transmission) of the lens. This state corresponds to the state having the highest specified shade number for the lens. The invention is described below in some instances indicating that in the dark state no light is transmitted. While this may be desirable for some applications of the principles of the invention, it will be appreciated that for a welding lens in the dark state there will be some transmission so that the welder can see to do the welding while some light is blocked to provide the desired eye protection from damage, injury or the like by the light emitted during welding.

Shutter response time is the time required for the circuitry associated with the lens to detect a sharp increase in incident light (e.g., due to striking of the welding arc, etc.) and to switch the lens from the clear state to the dark state.

Shutter recovery time is the time required for the circuitry associated with the lens to detect a sharp decrease in light (e.g., due to extinguishing of the welding arc, etc.) and to switch the lens from the dark state to the clear state.

Variable transmittance is the ability of the lens to be switched from one level of luminous transmittance (also referred to as transmission of light) to another level of luminous transmittance in response to a change in incident illumination.

Dynamic operational range or dynamic optical range of the welding lens or shutter is the operational range of the lens between the dark state and the clear state, e.g., the difference between the shade numbers of the dark state and the clear state.

Prior photosensitive devices and circuits for use in automated welding lens systems have not had sensor operational range to function well in both indoor environments and outdoor environments, and they were not automatically adjusting to the relatively gradual changes in ambient light compared to rapid change due to initiation of a welding arc, flame, etc. For example, the difference in light intensity between indoor ambient light and welding light is larger than the difference in light intensity between bright sunlight and welding light, and prior sensor devices and circuits were not able automatically and conveniently to adjust for such different ambient conditions. Prior sensor devices and circuits also did not adjust automatically to accommodate the change in ambient conditions when the door to a room is opened to allow bright sunlight to enter the room and possibly falsely to trigger a detection of welding or to impede proper sensitivity to welding.

It is desirable to minimize the time required for a drive circuit to energize variable liquid crystal shutters to a particular state, e.g., the dark state to expedite protection for a welder's eyes. Using such shutters in a welding helmet and in other environments where there is not a convenient access to a power supply connection directly to a utility company, battery power ordinarily must be used to drive the shutter. It is desirable to minimize the power drain on such battery or other portable power supply for such lenses and other devices to maximize safe long term operation without having to change a battery. It also is desirable to provide a wide dynamic sensor operational range for the photosensitive detector and associated circuitry for an automatic shutter.

BRIEF SUMMARY OF THE INVENTION

The present invention provides a driving circuit for a liquid crystal shutter or for other devices that reduces the power drain on a portable power supply. The invention also has the characteristic of fast response time. The invention further provides a sensor and sensor electronics which provide a wide sensitivity range which is automatically adjustable, and which has the ability to detect point sources of light. Additionally, the invention provides a low battery power indicator.

According to one aspect of the invention, a power supply for a liquid crystal shutter includes input means for providing an input representative of a desired optical characteristic of such shutter (e.g., clear, dark or other state or condition thereof), output means for supplying an electrical driving signal to such shutter to cause such optical characteristic thereof, power circuit means for selectively supplying to such output means a drive signal of selected power (e.g., electric field voltage) as a function of the input from the input means, and wherein when switching to the higher energy dark state of the shutter an initial high voltage electric field is supplied to expedite switching to the dark state and thereafter reduced voltage adequate to maintain the dark state is supplied.

According to another aspect of the invention, a power supply for a liquid crystal shutter includes input means for providing an input representative of a desired optical characteristic of such shutter (e.g., clear, dark or other state or condition thereof), output means for supplying an electrical driving signal to such shutter to cause such optical characteristic thereof, such output means being operative to provide a relatively low energy signal (e.g., electric field voltage) to obtain or a clear state of the shutter and a higher energy level to obtain the dark state, power circuit means for selectively supplying to such output means a drive signal of selected power (e.g., electric field voltage) as a function of the input from the input means, and wherein when switching to the higher energy dark state of the shutter an initial high voltage electric field is supplied to expedite switching to the dark state and thereafter reduce voltage adequate to maintain the dark state is supplied.

A number of power saving features are provided in the present invention to expand the useful life of the battery, for example, as used in a portable welding lens system.

One power saving feature is an automatic time-out circuit which turns off the welding lens power supply when it has been inactive for a period of time and a resetting of the time-out period in response to an initial energization of the supply and/or during welding.

Another power saving feature is the conservation of energy provided by driving the welding lens at a relatively high frequency to avoid flicker when in the clear state and reducing the driving frequency for increased power use efficiency when in a dark state.

Still another power saving feature is the efficient use of relatively high voltage to initiate expeditiously a dark state condition followed by the use of a reduced voltage to maintain the dark state.

Another aspect of the invention is a low battery voltage indicator to indicate when battery voltage is low and the battery should be changed.

A further aspect is an improved sensor and sensor electronics for use in a welding lens power supply or other device, wherein a variable light input threshold and feedback sensitivity control are provided to maintain high sensitivity in a wide range of ambient light conditions.

Various features of the invention, as are described herein, may be employed in optical shutters and in connection with other devices, too.

The foregoing and other objects, features, aspects and advantages of the present invention will become more apparent as the following description proceeds. It will be appreciated that while a preferred embodiment of the invention is described herein, the scope of the invention is to be determined by the claims and equivalents thereof.

Also, it will be appreciated that the power supply circuit described in detail below includes a number of features, which preferably are useful together and which also may be used independently in other circuits and devices.

To the accomplishment of the foregoing and related ends, the invention, then, comprises the features hereinafter fully described in the specification and particularly pointed out in the claims, the following description and the annexed drawings setting forth in detail a certain illustrative embodiment of the invention, this being indicative, however, of but one of the various ways in which the principles of the invention may be suitably employed.

DESCRIPTION OF THE PREFERRED EMBODIMENT

Figure 1:
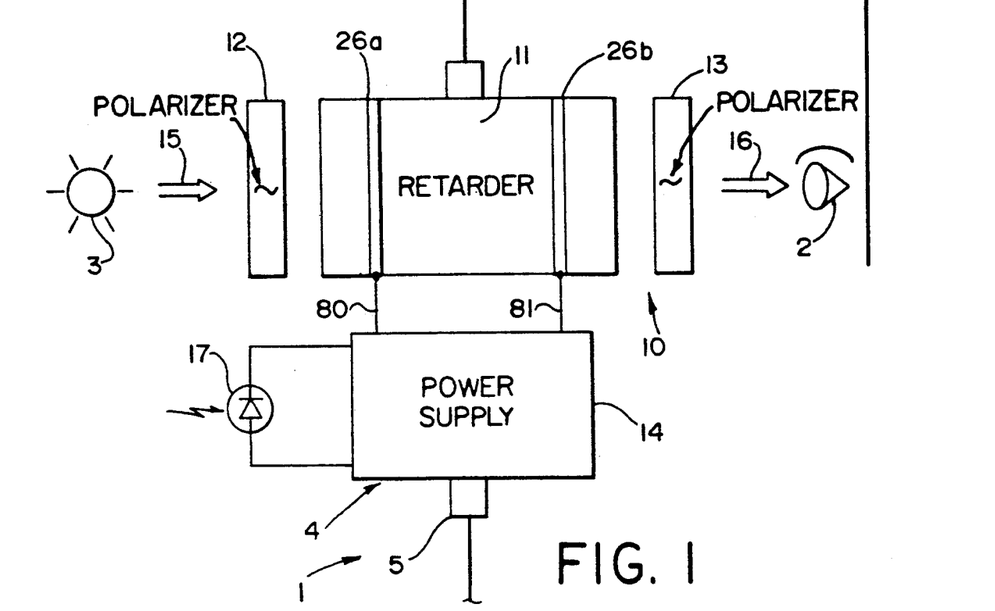
FIG. 1 is a schematic illustration of a liquid crystal optical shutter used in a welding helmet with a driving circuit therefor in accordance with the present invention.

Referring in detail to the drawings, wherein like reference numerals designate like parts in the several figures, and initially to FIG. 1, a welding helmet 1 for wearing on the head of a person to protect the eyes 2 of a person from bright light emitted by a welding process represented as light source 3 is illustrated. Mounted in an opening 4 by a mounting mechanism 5 is an exemplary welding lens or liquid crystal shutter 10, which includes a variable optical retarder 11 sandwiched between a pair of linear polarizers 12, 13. The optical axes of the polarizers 12, 13 may be at right angles to each other and at 45 degrees to the optical axis of the retarder 11 as is described in the above-mentioned patents and patent application. The retarder 11 may be of the type disclosed in the above-mentioned patents and patent applications. The shutter 10 may be used as a lens in a welding helmet, goggles or other eye protection device as well as in other devices intended to be protected from light or other electromagnetic energy which can be attenuated by the shutter. The shutter 10 may be a part of a welding lens system such as the ones disclosed in the above mentioned patent application.

A power supply 14 according to the invention is operative to provide an electric field of prescribed voltage to the retarder 11 to determine how much of the input light 15 is transmitted as output light 16 by the shutter 10. A photosensitive detector 17, for example, in the form of a photosensor arrangement, such as one or more silicon photodetectors (although other photosensors may be used), detects the intensity of the incident light 15 and provides a control input to the power supply 14 which automatically operates the shutter 11. Accordingly, when welding is not detected, input light 15 is at relatively low intensity, and substantially all of the light possible will be transmitted by the shutter 10 as output light 16. It will be appreciated that since polarizers and possibly other optical components are used in the shutter 10, it is likely that approximately 50% or more of the incident light 15 will be blocked by such polarizers in the clear state, as is described in the above referenced patent application. On the other hand, when welding is detected, the driving circuit 14 operates the shutter 10 to reduce substantially below 50% the relative intensity of the output light 16, i.e., relative to the intensity of the incident light 15, e.g., to several percent, preferably less than 1%, and more preferably to even less.

It will be appreciated that various types of photosensitive detectors and associated circuitry may be used in connection with the power supply 14 and liquid crystal shutter 10 in addition to that which is described in detail herein. It also will be appreciated that other types of detectors or sensors may be employed to provide an input or to provide information to the power supply circuit 14 to cause appropriate operation of the liquid crystal shutter 10. Examples are electrical sensors which sense the electrical energy used to undertake welding and temperature sensor that may be used to sense the change in temperature due to welding. Another sensor would be a flow sensor that detects the flow of a gas used during a welding process. Other types of sensors also may be used, as will be appreciated by those having ordinary skill in the art.

Figure 2A:
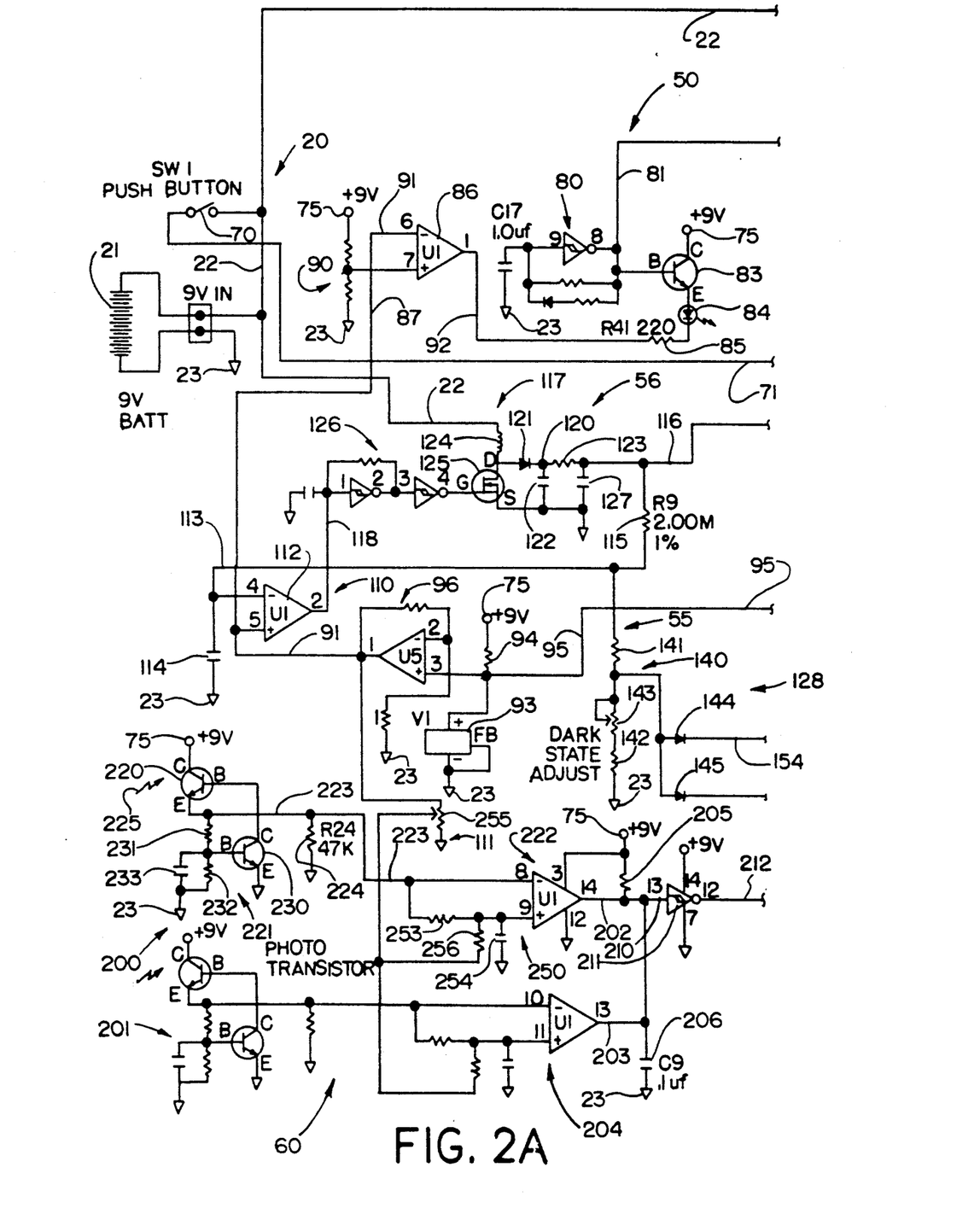
FIGS. 2A-2C are a schematic electric circuit diagram of a driving circuit employing the driver electronics according to the invention used with the liquid crystal shutter of FIG. 1.
Figure 2B:
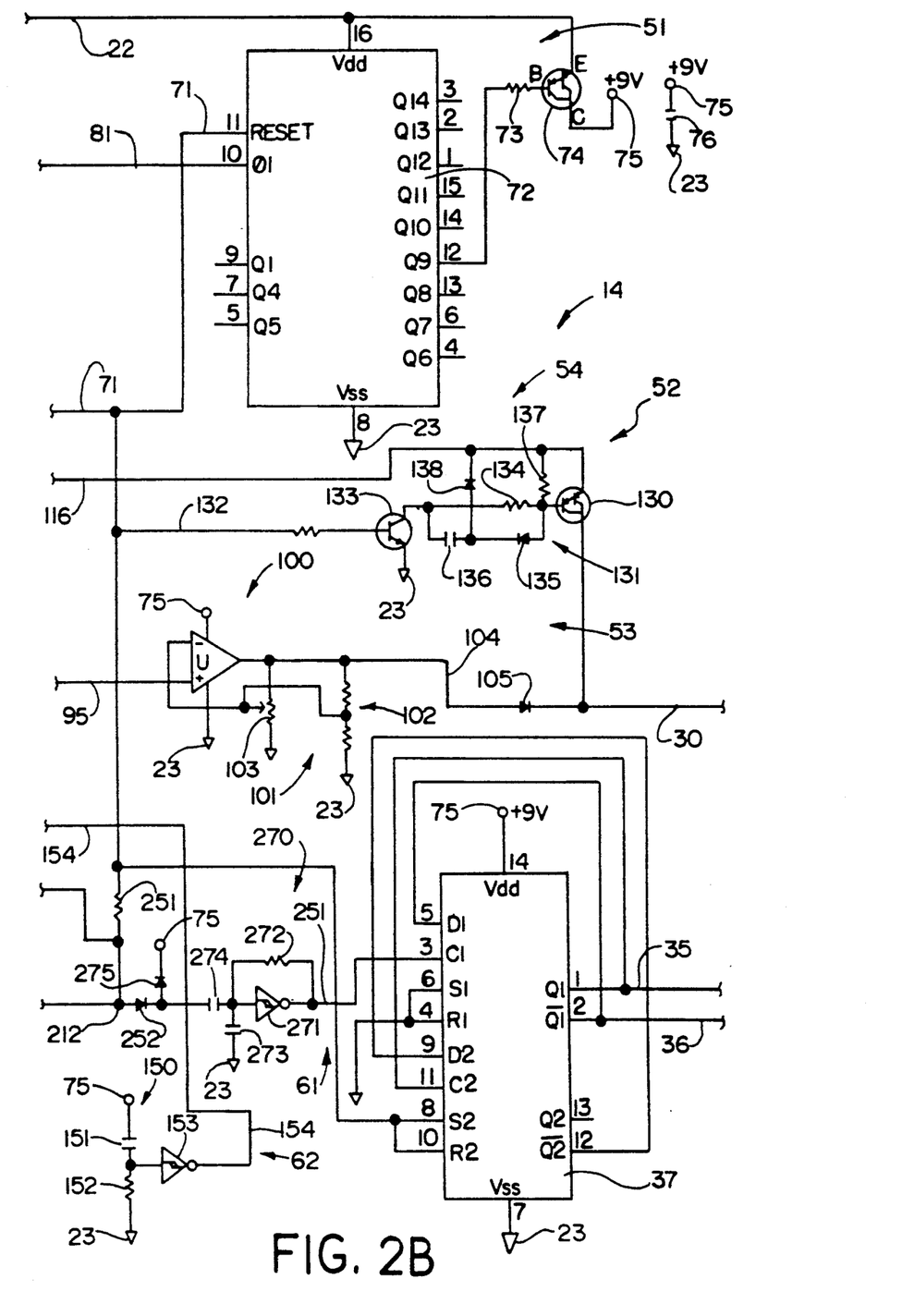
Figure 2C:
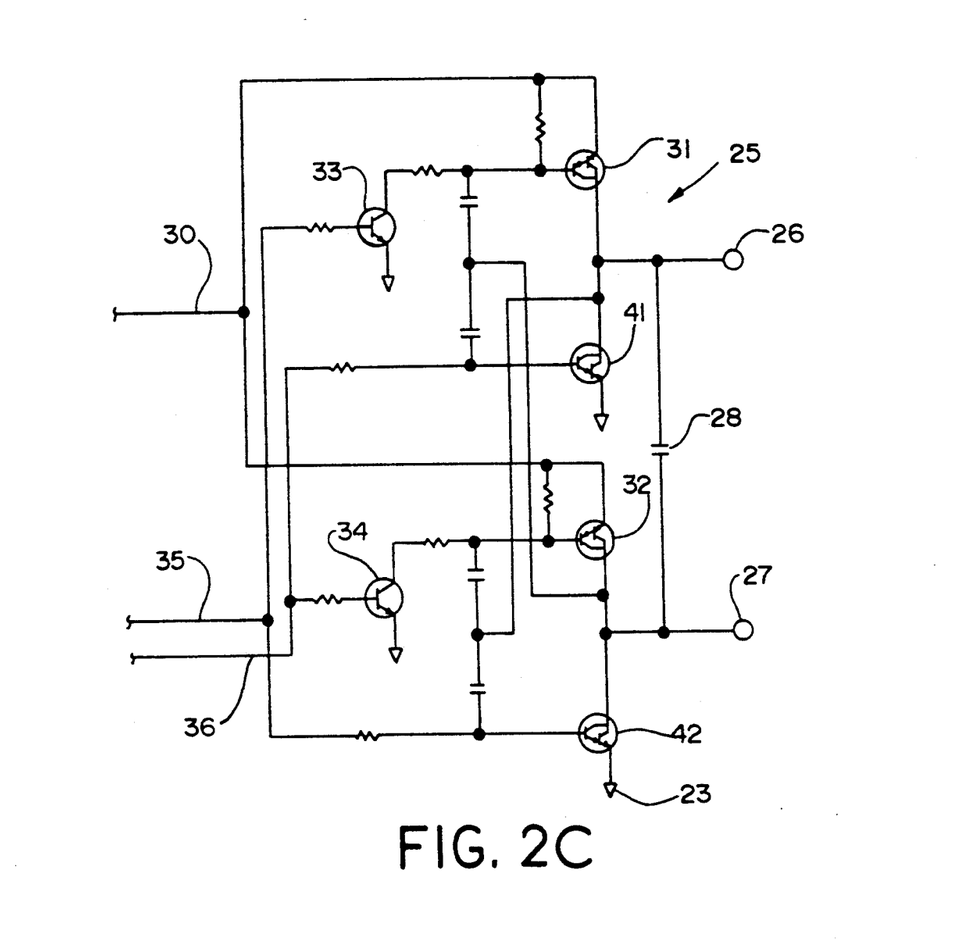

Turning to FIGS. 2A-2C, a schematic electric circuit diagram of the power supply circuit 14 is illustrated. The power supply 14 includes an input circuit 20 where input electrical power is provided the power supply 14, for example, from a 9 volt electrical storage battery 21, which is connected between a positive electrical line or connection 22 and a negative or relative ground potential line or connection designated 23 at the left hand side of FIG. 2A and elsewhere in the drawing. Other types of power supplies also may be used having larger or smaller magnitudes than the 9 volt battery indicated. Also, if desired, the power supply may be provided via a transformer connection and/or via a direct connection to a source of electrical power, such as a battery, alternator, generator, the electrical lines from the utility company, etc.

In the description hereof, reference to lines, leads, conductors, etc., essentially means an electrically conductive path from one place or device to another regardless of whether a discrete electrical wire is used for effecting the electrical connection; a printed circuit electrically conductive trace on a printed circuit board is employed to make that connection; implementation is within an integrated circuit where the connection is made; etc., without limitation. Furthermore, reference to logic 0 signal, ground reference potential, negative signal, etc., typically means the same, for example, a connection to the ground terminal 23 associated with the battery 21, or a typical logic 0 signal, as is well known in the electronics and digital circuitry field. Reference to a logic 1 signal typically means a positive (or negative, as the case may be) signal, such as that at the positive side of the battery 21, such as 9 volts, or some other relatively reduced value, but in any event a value that is distinguishable from the logic 0 signal level. These conventions are, of course, well known in the electronics art. Other conventions also may be employed consistent with the spirit and scope of the present invention.

Power Output Circuit 25

The power supply 14 also includes a power output circuit 25. The power output circuit 25 has a pair of terminals 26, 27, which are interconnected by a capacitor 28 in conventional fashion, that are coupled to electrodes or the like which provide operating energy or power to the variable optical retarder 11 (or other liquid crystal device, or still other device, in general) of the liquid crystal shutter 10. Typically an AC electrical voltage is supplied across the terminals 26, 27, and those terminals are connected to electrodes 26a, 26b that are at opposite sides of the variable optical retarder 11, for example, to provide an electric field across the liquid crystal material in the retarder. The power output circuit 25 is operated in a push pull fashion, as is described below.

More particularly, the power output circuit 25 includes an input power line or connection 30, which delivers to the power output circuit 25 a relatively low voltage signal for maintaining the liquid crystal shutter in the clear state or a relatively high voltage electrical signal for driving the liquid crystal shutter 10 to the dark state. The voltage provided on input power line 30 is delivered to the emitter inputs of two Darlington Pair transistors 31, 32 in the power output circuit 25. Conduction or a closure of connection between the emitter and collector of the respective Darlington Pair transistors 31, 32 is a function of the signals applied to the respective base of each; and that signal to the respective base is provided via a respective control transistor 33, 34. Further, control signals to the respective base of transistors 33, 34 are supplied via leads 35, 36, which are the respective complementary (opposite) outputs from a conventional flip-flop circuit 37, namely, terminals $Q_1$ and $Q_1$ (bar) from the flip-flop. When the line 35 is at a positive electric potential or voltage (e.g., logic 1), the line 36 is at a zero, ground or negative potential (e.g., logic 0); and vice versa, as is well known with respect to those complementary outputs of a conventional flip-flop circuit. The Darlington Pair transistors 31, 32 are coupled in a fashion to provide the voltage from input power line 30 to the respective terminals 26, 27; and further Darlington Pair transistors 41, 42 also are coupled to the terminals 26, 27 to provide a connection therefor to ground 23 or some other source of reference potential. Control signals to "turn on" to conduction the Darlington Pair transistors 41, 42 are supplied via connections to the respective leads 36, 35 from the output of the flip-flop circuit 37.

In operation of the power output circuit 25, then, when the signal on line 35 is positive, logic 1, etc., transistor 33 turns on to turn on Darlington Pair transistor 31 so that the voltage from the input power line 30 is coupled to the terminal 26; simultaneously, the logic 1 signal on line 35 is supplied to the base of the Darlington Pair transistor 42, which turns on to connect the terminal 27 to ground 23. Meanwhile, the logic 0 or negative signal on line 36 is supplied to the base of Darlington Pair transistor 41 so that it is not conducting and also is supplied to the base of transistor 34, which prevents the Darlington Pair transistor 32 from conducting. Thus, the terminal 26 is relatively positive compared to the terminal 27, and an electric field then is applied by the electrodes 26a, 26b across the liquid crystal material in the variable optical retarder 11 of the liquid crystal shutter 10. Reversal of the signals on lines 35 and 36, namely providing a logic 0 on line 35 and a logic 1 on line 36, results in opposite operation of the power output circuit 25, whereby the Darlington Pair transistors 31 and 42 are nonconductive, and the Darlington Pair transistors 32, 41 are conductive so that the terminal 27 is positive relative to the terminal 26. As the signals on lines 35 and 36 vary cyclically between logic 1 and logic 0 levels, an AC output signal will be supplied across the terminals 26, 27; the frequency of that signal will be a function of the frequency of the signals on lines 35, 36, and the voltage of that signal will be a function of the voltage on the input power line 30. Lines 35 and 36 provide inputs to the power output circuit 25 to drive the variable retarder 11 in the manner described above. Various resistors and capacitors are provided for signal coupling, wave shaping, etc., in conventional manner in the power output circuit 25.

The power supply circuit 14 includes a number of portions which are operational in response to receiving power from the input circuit 20 to derive the voltage on the input power line 30 and the complementary alternating signals on lines 35, 36 to operate the power output circuit 25, which in turn drives the liquid crystal shutter 10. A number of those portions include a low supply voltage indicator circuit 50; time out circuit 51; power developing circuit 52, which includes a low voltage drive circuit 53 and a high voltage drive circuit 54, that provides the voltage on input power line 30; a regulated low voltage power supply and voltage reference circuit 55; a high voltage power supply 56; a sensor circuit 60; a frequency varying circuit 61 for determining the frequency of the flip-flop 37 and the alternating complementary signals on lines 35, 36 coupled to the output thereof; and a start/initialization circuit 62. These various circuits and circuit portions will be described in greater detail below.

The description herein is directed to use of the power supply circuit 14 for developing a relatively low voltage AC signal for driving or powering the liquid crystal shutter 10 to the clear state and two relatively higher or larger magnitude AC electrical signals for initially driving the shutter to the dark state and then for maintaining the shutter in the dark state. The circuit also provides for varying the frequency of the driving signal to the shutter to minimize power usage in the dark state and to avoid flicker in the clear state. However, various features of the power supply circuit 14 may be used for providing power to operate other types of liquid crystal devices, such as shutters, displays or other devices; devices other than liquid crystal ones, and so forth.

Input Circuit 20, Low Supply Voltage Indicator Circuit 50, and Time Out Circuit 51

The input or start circuit 20 includes a momentary contact switch 70, which is coupled between positive line 22 (positive because it is coupled to the positive terminal of the battery 21) and to a reset input line 71 of a counting circuit (integrated circuit) 72 of the time out circuit 51. A brief closure of the switch 70 resets the counting circuit 72 to provide an output on line 73 to effect closure of or conduction through a Darlington Pair transistor 74. Conduction by the transistor 74 provides the battery voltage on line 22 to the $V_{cc}$ power terminal 75 of the circuit. Such terminal 75 preferably is coupled to the various $V_{cc}$ or other positive power input terminals illustrated elsewhere in the circuit as shown in the drawing to provide battery voltage there. Moreover, preferably a capacitor 76 is coupled to the terminal 75 to filter the voltage there, as it is supplied to other portions of the circuit; such filtering being conventional.

For the low supply voltage indicator circuit 50 and time out circuit 51, a free running oscillator circuit 80 provides an AC signal, for example a square wave signal, on line 81, which is delivered to an input of the counting circuit 72. Power and ground connections are supplied the counting circuit 72 as is indicated. The counting circuit 72 may be a conventional integrated circuit that provides an output signal on the respective outputs, for example, on output 73, thereof as a function of the number of AC signal pulses or the like delivered to the input 82 thereof. In one embodiment, the frequency of the signal produced by the oscillator 80 and, (after it has been reset by a signal on line 71) the number of pulses (counts) having to have been received by the counting circuit 72 in order to produce an output on line 73 are selected to take a prescribed period of time, for example, about 15 or 16 minutes. If the counting circuit 72 reaches the prescribed number of counts before being reset by a signal on line 71, then the signal on line 33 causes the Darlington Pair transistor 74 to stop conducting, thereby to remove the battery voltage from the terminal 75 and to deenergize the power supply circuit 14. Therefore, it will be appreciated, that if the power supply 14 initially is energized by closing the switch 70, but welding is not occurring, the time out circuit 51 automatically will turn off the power supply 14 after the prescribed time that is determined as a function of the frequency of the signal produced by the oscillator 80 and the number of counts required by the counting circuit 72 to provide an output on line 73 thereof. If welding is being detected by the sensor circuit 60, a reset signal will be delivered to line 71 by the sensor circuit until welding no longer is being detected.

Still referring to the low supply voltage indicator circuit 50 and time out circuit 51, the line 81 at the output of oscillator 80 is coupled to the base of a transistor 83. The collector and emitter junction of the transistor 83 is connected between the circuit power terminal 75 and a light emitting diode 84. The diode 84 in turn is connected via a resistor 85 to the output of a comparator amplifier 86.

The comparator 86 receives the battery voltage from terminal 75 via a resistor divider circuit 90 that is coupled to the non-inverting input and a regulated voltage on line 91, which is supplied from the regulated low voltage power supply and voltage reference 55 to the inverting input. The regulated voltage on line 91 is accurately maintained by the circuit 55 to a prescribed level. As long as the battery voltage at terminal 75 is of adequate magnitude, the comparator 86 will produce a logic 1 signal at its output 92 to block conduction through the diode 84. However, if the battery voltage at terminal 75 drops below a minimum magnitude, which is determined by the resistor divider 90 and the magnitude of the signal on line 91, the output from the comparator 86 switches to a logic 0 level (or effectively to ground reference potential), whereupon conduction through the diode 84 is unblocked. In the latter circumstance the oscillating signal on line 81 will cause the transistor 83 in the low supply voltage indicator circuit 50 to oscillate between conduction and non-conduction, whereupon an oscillating current will flow through the diode 84 causing the diode 84 to emit a blinking light output. Such blinking light output indicates that the voltage magnitude provided by the battery 21 is below minimum magnitude for proper operation of the power supply circuit 14.

In the regulated low voltage power supply and voltage reference circuit 55 a voltage reference device 93 is connected in circuit with the battery terminal 75, resistor 94, and ground 23. The voltage reference device may be an LM385 which produces a 1.23 volts output; or it may be another device which provides the same or a different regulated voltage output. An alternate device might be a zener diode. The voltage on line 95 is relatively accurately regulated by the reference 93, and such regulated reference voltage is supplied both via an amplifier 96 to line 91 and directly via line 95 to an input of the low voltage drive circuit 53.

Low Voltage Drive Circuit 53

In the low voltage drive circuit 53 an amplifier 100 receives the regulated reference voltage on line 95. The amplifier 100 has a feedback circuit 101, which includes a resistor divider 102 and an adjustable potentiometer (variable resistor) 103. In response to the regulated reference voltage input on line 95 and adjustment of potentiometer 103, the amplifier 100 produces on its output line 104 a voltage (e.g., from about two volts to about four volts) that is of a magnitude intended to maintain the shutter 10 in the clear state. The potentiometer 103 may be adjusted manually (or otherwise) to adjust the actual voltage on line 104 so that such voltage is the desired voltage for maintaining the clear state of the shutter 10. The voltage on line 104 is supplied via blocking diode 105 to the input power line 30. The blocking diode 105 prevents voltage from the high voltage drive circuit 54 from feeding to the low voltage drive circuit 53. Ordinarily it is expected that the voltage on line 95 will be maintained relatively accurately as a function of the voltage reference 93 as long as the voltage at battery terminal 75 exceeds a minimum voltage value. If the battery 21 does not supply the minimum voltage value, then the low supply voltage indicator circuit 50 will cause the diode 84 to flash.

The amplifier 96 boosts the reference voltage signal from the regulated voltage source 93 received on line 95. The amplifier 96 also provides adequate sourcing capability to provide the necessary input to three circuits in the power supply 14, as is described below. The regulated voltage on line 91 at the output from the amplifier 96 is supplied to the comparator 86 in the low supply voltage indicator circuit 50. The regulated voltage on line 91 also is supplied to a comparator input circuit 110, which is associated with the high voltage power supply 56. The regulated voltage on line 91 further is coupled via an adjustable potentiometer 111 to the sensor circuit 60, as is described further below.

High Voltage Power Supply 56 and High Voltage Drive Circuit 54

The comparator input circuit 110 to the high voltage power supply 56 includes a comparator amplifier 112, which has its non-inverting input coupled to line 91 to receive the amplified regulated voltage, and which has its inverting input coupled to line 113. Line 113 is coupled via a capacitor 114 to ground 23 and via a resistor 115 to the power output line 116 of a high voltage switching DC to DC power supply circuit 117. When the voltage on line 113 is less than the voltage on line 91, the comparator amplifier 112 produces a signal on line 118 to energize the switching power supply 117 to develop a relatively high voltage level at the junction 120 of a diode 121, capacitor 122 and resistor 123, as is seen in FIG. 2. Preferably the high voltage power supply 56 receives the 9-volt battery voltage on line 22 and it is operative using the inductor 124, field effect transistor (MOSFET) 125, diode 121, capacitor 122, and input amplifier circuit 126 to develop at the junction 120 a relatively high voltage signal suitable to drive the shutter 10 in the dark state. Capacitor 114 adds stability to the circuit by decoupling noise on line 113 from reaching the comparator 112.

More particularly, the high voltage power supply circuit 56 uses the input amplifier circuit 126 to develop a square wave signal, for example at 100 KHz to drive the MOSFET 125 to provide rapid switching for the inductor 124. A voltage developed by the inductor 124 and transistor 125 is delivered via the diode 121 for storage in the capacitor 122. Resistor 123 and capacitor 127 provide an RC filter and storage function. The inductor 124 charges the capacitor 122 through the diode 121 as a conventional LC circuit; and the capacitor 122 tends to maintain a voltage level thereon at about 40 volts or at some other voltage determined by a dark state adjustment resistance divider circuit 128, as is described below. The actual magnitude of the signal on line 116 at the output of the high voltage power supply circuit 56 can be adjusted as a function of the magnitudes of the various components in the circuit, as will be appreciated by those having ordinary skill in the art and as is described further below.

Moreover, a power saving feature of the high voltage power supply circuit 56 is that operation thereof to develop the relatively high voltage on line 116 only occurs when the comparator input circuit 110 detects that the voltage on line 116 is too low relative to the regulated low voltage on line 91. Therefore, the high voltage power supply 56 only is operated when it is needed to provide or to boost the voltage on line 116.

The high voltage on line 116 is selectively coupled to the input power line 30 via the high voltage drive circuit 54. The high voltage drive circuit 54 includes an output Darlington pair transistor 130 and a control circuit 131 therefor. The control circuit 131 receives a signal on line 132 to the base of a transistor 133 when it is desired to provide the high voltage from line 116 to the input power line 30 in order to drive the shutter 10 to the dark state. The control circuit 131 includes a resistor 134 that is coupled between the collector of transistor 133 and the base of the Darlington pair transistor 130; and it also includes a diode 135 and a capacitor 136. A resistor 137 is coupled between the line 116 and the base of the Darlington pair transistor 130. A diode 138 couples the junction of the diode 135 and capacitor 136 to the high voltage line 116.

In operation of the control circuit 131, in the absence of an appropriate signal on line 132, such as a logic 1 level signal or some other positive signal, the transistor 133 is not conductive, and the Darlington pair transistor 130 is not conductive. Therefore, high voltage from line 116 will not be delivered to the input power line 30. However, when a signal is provided line 132 indicating a call for high voltage to be supplied to the input power line 30 to cause the shutter 10 to assume the dark state (being powered to a high voltage applied across the terminals 26, 27 of the power output circuit 25), the transistor 133 becomes conductive, and the Darlington pair transistor 130 promptly becomes substantially fully conductive. Therefore, the full voltage on line 116 is delivered the input power line 30. Diode 105 blocks coupling of the relatively high voltage on the input power line 30 from reaching the low voltage drive circuit 53.

The capacitor helps to pull down (in voltage or potential) the base of the Darlington Pair Transistor 130 immediately when the transistor 133 turns on. This overcomes capacitance in the Darlington Pair transistor 130 and helps to speed up the turn on to conduction of the Darlington Pair transistor. Diodes 135 and 138 eliminate voltage spikes from the circuit. Diode 135 prevents the capacitor 136 from turning off the Darlington Pair transistor 130. Diode 138 drains voltage from the capacitor 136. Moreover, after the capacitor 136 has helped to turn on the Darlington Pair transistor 130, such transistor will be maintained on a conductive by current from the resistor divider circuit including resistors 134, 137 while the transistor 133 remains conductive. Ordinarily the current required to maintain the Darlington Pair transistor 130 conductive is less than that required initially to turn it on; by reducing the base signal using the resistors 134, 137 some power is saved in the circuit 14. Exemplary values for the resistors 134, 137 and the capacitor 136 may be, for example, 2 megohms for each of the resistors and 470 pf for the capacitor.

The high voltage power supply circuit 56 is operative initially to provide via the high voltage drive circuit 54 a high voltage to the variable retarder in the shutter 10 to expedite transition to dark state. Thereafter, a reduced voltage that is adequate to maintain the dark state is provided to the shutter by the circuits 56 and 54. Such dark state maintaining voltage, though, ordinarily would be greater than low voltage provided at the output of the low voltage drive circuit 53, which is used to maintain the clear state for the shutter 10.

The dark state adjustment circuit 128 includes the resistor 115, which is coupled to the high voltage line 116, and also includes resistors 141, 142 and adjustable potentiometer 143. By adjusting the potentiometer 143, and, thus, the total resistance in the resistor voltage divider circuit formed by the resistor 115 and resistors 141, 142, 143, the value of the voltage on line 113 at the inverting input to the comparator 112 relative to the actual voltage on high voltage line 116 can be adjusted. Accordingly, such adjustment determines the operation of the comparator 112 as it compares the voltage on line 113 to the inverting input with the regulated voltage on line 91 to the non-inverting input. Adjustment of the potentiometer 143 effectively adjusts the magnitude of the regulated high voltage on the high voltage line 116 for maintaining the dark state of the shutter 10 after it initially is driven to dark condition.

To determine the magnitude of the voltage at line 116 from the high voltage power supply 56, the dark state adjustment circuit 128 can be selectively switched by selective blocking or unblocking of diodes 144, 145. When the cathode of either diode 144, 145 is coupled to a source of ground reference potential, such diode is unblocked. Such unblocking may be provided by the start/initialization circuit 62 or by the sensor circuit 60. If either diode 144, 145 is unblocked, then it effectively short circuits or bypasses the potentiometer 143 and resistor 142. Therefore, for a given voltage on line 116, the voltage on line 113 will be less than it would be if such potentiometer 143 and resistor 142 were not bypassed. Accordingly, the comparator 112 will operate the high voltage power supply circuit 56 to strive to produce a maximum voltage at output junction 120, at, for example, from about 30 volts to about 50 volts, preferably about 40 volts.

However, when both diodes 144, 145 are blocked by logic 1 signals at their cathodes, the potentiometer 143 and resistor 142 are operatively in circuit with the resistors 115, 141; and the proportion of the voltage on line 116 which appears on line 113 increases. Therefore, the voltage produced at the output junction 120 and on line 116 is reduced to from about 10 volts to about 25 volts, preferably about 19 volts. The storage capacity of the capacitor 127 prevents immediate change between the very high, say 40 volts, and lower, say 19 volts, output from the high voltage power supply circuit 56.

The high voltage 40 volt signal expedites switching of the shutter 10 to the dark state. The lower voltage 19 volt signal is adequate to maintain the dark state thereafter. The voltage reduction reduces power draw on the battery 21. It will be appreciated that the high voltage and maintenance voltage may be other than those described herein, e.g., depending on circuit component values, shutter requirements, etc.

The start/initialization circuit 62 includes an RC charging circuit 150 that has a capacitor 151 and resistor 152 coupled in series across the positive battery terminal 75 and ground 23. A Schmitt trigger circuit 153 is coupled between the capacitor 151 and resistor 152. The output 154 from the Schmitt trigger circuit 153 is coupled via a diode 144 to the junction between the resistor 141 and potentiometer 143 in the dark state adjustment circuit 128. When the pushbutton switch 70 is closed initially to start operation of the power supply circuit 14, a high voltage input to the Schmitt trigger circuit 153 produces a low voltage or logic 0 signal on line 154 closing conduction through the diode 144 effectively directly to ground reference potential bypassing the potentiometer 143 and resistor 142. Therefore, line 113 tends to be pulled toward a lower voltage than it would be if the potentiometer 143 and resistor 142 were in circuit connection therewith; and, therefore, the high voltage power supply 56 strives to produce a maximum voltage on the high voltage line 116. Such maximum voltage is available, then, when the power supply 14 initially is turned on so that the shutter initially is driven at high voltage (e.g., 40 volts) to the dark state in order to set up all of the liquid crystal director or alignment structure in the variable retarder 11 of the shutter 10 at the outset of operation. After the capacitor 151 adequately charges, the output from the Schmitt trigger 153 reverts to logic 1 to block the diode 144. If at that time the diode 145 were blocked, then, the voltage at line 116 would revert to the dark state "maintenance" level of, for example, 19 volts. The time for such charging of the capacitor 151 may be on the order of one fourth second. Other times also are possible, as will be appreciated to those having ordinary skill in the art. (If the diode 145 were unblocked, though, the higher voltage would remain at the output line 116 of the high voltage power supply circuit 56.)

Sensor Circuit 60

The sensor circuit 60 includes a pair of photosensitive or photodetector circuits 200, 201, which are electrically connected together at lines 202, 203 as an OR gate 204. A resistor 205 and a capacitor 206, are coupled between the battery positive terminal 75 and ground 23, and lines 202, 203 are coupled to the junction of those resistor and capacitor. The capacitor 206 provides a dark to clear delay time of, for example, one fourth second (or other time period) so that a brief interruption in the welding light or some other brief loss of light detection will not allow the shutter to transition from dark state to clear state.

The output from the OR gate 204 is provided to input 210 of a Schmitt trigger circuit 211. When welding is not detected, it is intended that the signal on line 210 will be a logic 1 or relatively positive voltage so that the output from the Schmitt trigger circuit 211 provided on line 212 will be a logic 0 or relative ground signal. Conversely, when welding is detected, it is intended that the signal at the output from the OR gate 204 goes to a logic 0 level (or relative ground), which causes the signal on line 212 to go to a logic 1 or positive voltage level. Thus, a logic 1 signal on line 212 indicates a call for a dark state of the shutter 10.

The photodetector circuits 200, 201 preferably are identical, and, therefore, only one will be described in detail. The two circuits are provided for redundancy. If one fails to detect welding, it is expected that the other will detect welding. Alternatively, the circuits 200, 201 may be different types and/or use different photodetectors, etc. It is intended, thought, that if either photodetector circuit 200, 201 detects welding, i.e. the occurrence of light emitted by a welding arc, welding flame, etc., the signal at the output of the OR gate 204 provided on line 210 will go to a logic 0 level indicating welding.

The photodetector circuit 200 includes a silicon photodetector or phototransistor 220 (designated 17 in FIG. 1 and shown there as a photosensitive diode), a feedback circuit 221, and a comparator circuit 222. Other types of photodetectors also may be equivalently used as a substitute for the silicon photodetector transistor 220. The collector and emitter terminals of the photodetector 220 are connected between the battery positive terminal 75 and a line 223, which also is connected to the inverting input of the comparator 222. A load resistor 224 is coupled between the line 223 and ground 23. The photodetector 220 is responsive to incident light produced during welding and also to incident light due to other ambient lighting conditions, e.g., room light, sunlight, etc. It is intended that as the incident light 225 increases in intensity, the voltage on line 223 will increase; likewise a decrease in the intensity of light 225 will cause a decrease in the voltage on line 223 as a result of operation of the photodetector 220.

Two conventional types of welding produce welding light that have different characteristics: in one type of welding the welding arc is pulsating so that the welding light will be pulsating; and in other types of welding the welding arc or flame is continuous and does not pulsate so that the welding light is continuous as a DC type of signal. The photodetector 220 has an adequately fast response even to such pulsating welding light in which case the voltage on line 223 will be a pulsating one; and, in the case of the continuous welding light, the signal on line 223 will be substantially continuous.

The feedback circuit 221 includes a feedback transistor 230, a pair of resistors 231, 232, and a capacitor 233. The feedback circuit 221 is coupled to the base of the photosensitive transistor 220 to adjust the sensitivity of the photosensitive transistor 220. The resistors 231, 232 and capacitor 233 are chosen to be of a size to provide a relatively large time constant and, therefore, a relatively slow response to changes in the voltage on line 223. Exemplary values are 1 megohm for resistor 231, 270 k ohm for resistor 232, and 0.015 f for the capacitor 233. Rapid changes in the signal on line 223, e.g., due to a pulsating welding light, or due to initiation of a continuous welding light signal, will not have a significant impact on the feedback circuit 221 and will not cause a change in the sensitivity of the photodetector 220. However, for relatively slow or gradual changes in the intensity of the incident light 225, or after a period of time following a rapid change in incident light 225, the feedback circuit 221 will alter the sensitivity of the photodetector 220 by changing the signal to the base thereof so that the sensitivity of the photodetector will tend to track or to follow the brightness of the incident light.

Figure 3:
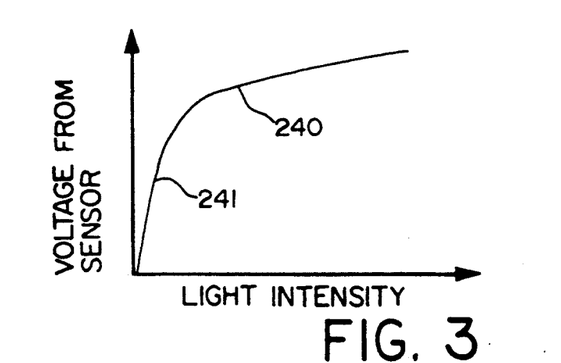
FIG. 3 is a graph showing the relationship of the conduction or voltage output characteristic of the photodetector in the circuit of the invention.

Briefly referring to FIG. 3, a graph showing the relationship of the conduction or voltage output characteristic of the photodetector 220 with respect to incident light 225 is illustrated. More specifically, the curve 240 represents the nonlinear response of the photodetector 220 if the feedback circuit 221 were connected to the base thereof. Specifically, the curve 240 represents the relationship between the voltage from the photodetector 220, which is on the vertical axis, relative to the intensity of the incident light 225, which is represented on the horizontal axis of the graph of FIG. 3. Such a nonlinear response is desirable when it is intended that the photodetector 220 be able to detect welding in environments that have a wide variation in ambient light intensity level, for example, indoor room ambient light compared to bright sunlight outdoors.

It is desirable to operate the photodetector 220 at the relatively steep slope portion 241 of the curve 240 in order to obtain a relatively fast detection of the existence of welding. By adjusting the sensitivity of the photodetector 220 with respect to gradual changes in the ambient light intensity by using the feedback circuit 221, this is accomplished. However, it will be appreciated that the response time of the feedback circuit 221 is intended to be adequately slow so that the inception of welding or the continuous pulsing of welding light will not cause an alteration in the sensitivity of the photodetector 220. It will be appreciated that the feedback circuit 221 in conjunction with the photodetector 220 provides a relatively large operating range between bright and dark ambient conditions for the sensor circuit 60 and, thus, for the power supply 14 and shutter 10. Thus, a relatively wide dynamic sensor operational range is obtained.

The comparator 222 in conjunction with the several inputs thereto provide a sensor threshold establishing and detecting circuit 250. When welding is not detected, it is intended that the circuit 250 produce on line 210 a logic 1 signal, which is inverted by the Schmitt trigger circuit 211 to produce a logic 0 signal on line 212. The logic 0 signal on line 212 unblocks diode 145 in the dark state adjustment circuit 128 so that the voltage produced at line 116 by the high voltage power supply circuit 56 is at a relative maximum, e.g., approximately 40 volts. The logic 0 signal on line 212 also operates via resistor 251 to block conduction by the transistor 133 and Darlington Pair transistor 130 in the high voltage drive circuit 54. Of course, no high voltage then is intended to be supplied to the input power line 30 because welding has not been detected. Furthermore, the logic 0 signal on line 212 blocks conduction through the diode 252 at the input to the frequency varying circuit 61, which then is producing a relatively high frequency of, for example, 40 hertz, signal on line 252 as an input to the flip-flop 37. Such relatively high frequency signal on line 252 is desired at this time because the shutter 10 would be operated in the clear state, as welding was not detected, and the high frequency signal on line 252 is desirable to avoid flicker, i.e., rapid transition in the variable retarder 11 that might be discernable visually.

The voltage on line 223 is provided to the inverting input of the comparator 222 in the threshold circuit 250. The voltage on line 223 also is provided via resistor 253 to the non-inverting input. A capacitor 254 is coupled between the non-inverting input and ground 23. The threshold voltage level setting potentiometer 111 is coupled between the output from amplifier 96 at line 91 and a resistor 256, which in turn is connected to the non-inverting input of the comparator 222 (and via the resistor 253 to the inverting input).

The several resistors and capacitor coupled to the non-inverting input of the comparator 222 set the voltage threshold level at which the comparator will trigger so as to produce a logic 0 signal at its output 202 indicative of detection of welding. Such voltage threshold is set by adjusting the potentiometer 111 to determine that portion of the regulated reference voltage on line 91 which is to be delivered via the resistor 256 to the comparator 222.

The voltage on line 223, as was mentioned above, is supplied to the inverting input of the comparator 222 and via the resistor 253 to charge the capacitor 254, both of which are coupled to the non-inverting input.

Figure 4:
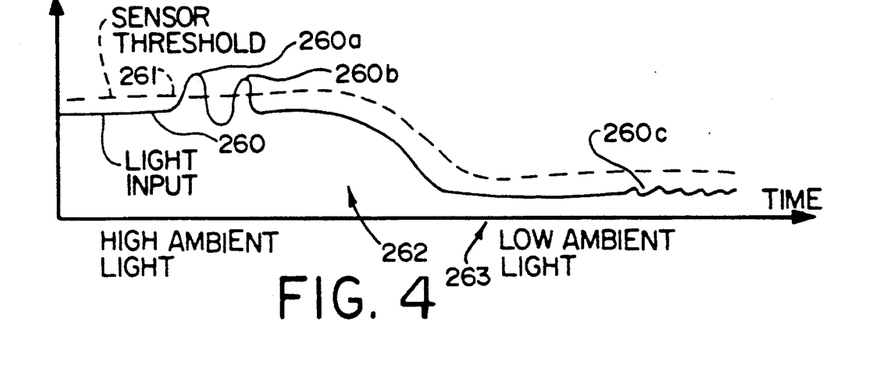
FIG. 4 is a graph representing the relationship between the intensity of incident light on the photodetector of the circuit of the invention and the variable threshold level developed in the circuit of the invention.

Briefly referring to FIG. 4, a graph, which includes two curves 260, 261 is illustrated. In the graph of FIG. 4, curve 260 represents the intensity of incident light 225 directed to the photodetector 220 and the signal that results on line 223. Fluctuations in the signal, for example at 260a, 260b may represent a rapid change in ambient light, for example upon the occurrence of welding. Fluctuations at the area 260c represent fluctuations, for example, due to opening of a door, window, etc. The curve 261 represents the sensor threshold voltage level which is set up by the relationship of the potentiometer 111, resistor 256, resistor 253, and capacitor 254, all providing input to the non-inverting input of the comparator 222. By adjusting the potentiometer 111, the closeness or separation of the curve 261 relative to the curve 60 can be altered. Also, the RC time constant for changing the capacitor 254 is relatively slow compared to the rapid changes that are expected to be detected during welding, in particular the pulsating light from the pulse type of welding operation.

From the graph of FIG. 4, then, it will be seen that the sensor threshold level represented by curve 261 generally tracks the curve 260 representing the signal on line 223 (intensity of incident light.) This occurs regardless of whether the photodetector 220 is exposed to a relatively high ambient light condition, e.g., due to bright sunlight entering a window of a room in which welding is being or is to be carried out, represented at the left hand portion 262 of FIG. 4 or to a relatively low ambient light condition, e.g., after the curtain, blind or shade is closed over window, represented at the right hand portion 263 of FIG. 4. Regardless of whether welding occurs at the high ambient or low ambient light level, perturbations in the light input curve 260, e.g., at 260a, 260b, which occur as a result of welding will exceed the sensor threshold level curve 261 so as to cause the signal at the inverting input of the comparator 222 to exceed that of the non-inverting input and to cause the comparator 222 to produce a logic 0 signal at the output 202 thereof indicating that welding is being detected. If the type of welding is that which produces a relatively continuous welding light, then the threshold setting potentiometer 111 can be adjusted to force the inverting input of the comparator 222 to remain generally at a higher voltage level than the non-inverting input by cutting down the voltage supply to the non-inverting input either at all times or at times when the intensity of the incident light 225 and voltage on line 223 exceed a predetermined substantially constant magnitude. In such case, the signal on line 202 will remain a logic 0.

Thus, it will be appreciated that the sensor circuit 60 is operative to detect welding in the manner described above. If the welding detected is of the type that produces a pulsed light, then such pulses, e.g., represented at 260a, 260b in FIG. 4, will trigger welding detection as long as those pulses exceed the threshold level represented by curve 261. If the welding produces a continuous light 225, then the potentiometer 111 may be adjusted to assume that welding will be detected as a function of the intensity of the light possibly even without the provision of a threshold function described above. When welding is detected a logic 0 signal is produced at the output 202 of the comparator 222; when welding is not detected, a logic 1 signal is produced at the output 202. The photodetector circuit 201 operates substantially identical to the photodetector circuit 200, and the output of the two photodetector circuits are connected in an OR gate arrangement 204 to provide the logic 1 or logic 0 signal at the output 202.

In the absence of welding being detected, a logic 0 signal is produced on line 212, which unblocks diode 145 so the voltage at line 116 will be charged to a maximum, e.g., 40 volts, which cuts off the high voltage drive circuit 54, and which blocks the diode 252. However, when welding is detected, a logic 1 signal on line 212 causes conduction or unblocks the diode 252, blocks the diode 145, turns on the high voltage drive circuit 54, and resets the counting circuit 72 and the time out circuit 51 via signal provided on line 71 thereto. Capacitor 206 provides a time delay of, for example, one fourth second (or some other time), to prevent constant detection and undetection of welding in the event that the pulsed type of welding light 225 occurs or the welder briefly turns is or her head from viewing the welding light or otherwise briefly loses a light path connection between the welding light and the photodetector 220. The time constant or changing period for the capacitor 206 may be other than one fourth second, e.g., either longer or shorter.

Frequency Varying Circuit 61

The frequency varying circuit 61 includes an oscillator 270 formed by a Schmitt trigger circuit 271, feedback resistor 272, and one or both capacitors 273, 274. The capacitor 273 is connected to ground 23.

When welding is not detected, the resistor 272 and capacitor 273 determine the time constant for the oscillator 270. Such time constant is relatively fast, for example, causing the oscillator 270 to produce an output signal having a frequency on the order of 40 Hz, although the actual frequency may be larger or smaller. Preferably the frequency is adequate to minimize power required for driving the shutter 10 while avoiding flicker. The output from the oscillator 270 is provided via line 252 as an input to drive the flip-flop 37.

When the sensor circuit 60 detects welding and provides a logic 1 signal on line 212, the diode 252 becomes conductive and effectively adds the capacitor 274 operatively in circuit connection with the capacitor 273 and resistor 272 for the oscillator 270. Adding such capacitor 274 in such circuit causes the oscillator 270 to reduce the frequency in the output signal produced thereby on line 252, e.g., to several Hz. The reduced frequency signal drives the flip-flop 37 at a reduced frequency so that the shutter is driven at a reduced frequency. As a result, the power required to drive the shutter is reduced. Also, since the shutter then is operating in the dark state, any problem due to flicker is avoided. Diode 275 connected to the battery positive terminal 75 provides for discharging of the capacitor 274 after welding no longer is detected by the sensor circuit.

SUMMARY OF OPERATION

When the momentary contact power switch is closed, the time out circuit 51 is reset to count for 15-16 minutes, and battery voltage is provided terminal 75 until the time out circuit shuts down the power supply circuit 14. If the voltage of battery 21 is below a prescribed minimum, the light emitting diode 84 will flash. Upon closing the switch 70, the start/initialization circuit 62 will unblock diode 144 so that the high voltage power supply circuit rapidly will charge to its maximum high voltage level of, say, 40 volts ready to drive the shutter 10 to the dark state. The closed switch 70 will turn on transistor 133 to conduction, which, in turn, turns on the Darlington Pair transistor 130; and the latter then supplies the high voltage from line 116 of the output of the high voltage power supply circuit 56 to the shutter 10 to set up the directors in the variable retarder 11. After the capacitor 151 in the start/initialization circuit 62 charges adequately so that the diode 144 becomes unblocked, if welding has not yet occurred, there will be a logic 0 signal at line 212 from the output of the sensor circuit 60. Such logic 0 signal maintains diode 145 unblocked so that the voltage at line 116 will remain at maximum; and such logic 0 also maintains the high voltage drive circuit 54 cut off. If welding has not yet been detected after the capacitor 151 charges adequately to disable the start/initialization circuit 62, then the low voltage drive circuit 53 provides a voltage through the diode 105 to maintain the shutter in the clear state. However, when welding subsequently is detected (or if welding were detected while the start-/initialization circuit still were in its initialization mode unblocking diode 144), a logic 1 signal is produced on line 212 to turn on the high voltage drive circuit 54, which then delivers the initial high voltage from line 116 to the power output circuit 25 to expedite turn on of the shutter to the dark condition. The logic 1 signal on line 212 also blocks diode 145 so that the voltage at line 116 will drop the reduced dark state maintenance voltage level to maintain the shutter in the dark state. The frequency of the shutter drive signal at terminals 26, 27 will be a function of the frequency varying circuit 61, which produces a high frequency signal when clear state is required and a lower (but non-zero to avoid polarizing the liquid crystal and/or other detrimental affects) frequency signal when dark state is required.

STATEMENT OF INDUSTRIAL APPLICATION

From the foregoing it will be appreciated that the power supply 14 is useful in energizing a variable retarder 11 in a welding lens shutter 10 used, for example, in a welding helmet or other eye protecting or device protecting apparatus.

We claim:

1. A detector system for detecting the occurrence of welding, comprising detector means for receiving a light input and producing an output representative thereof;
   feedback means coupled with respect to said detector means for tending to maintain substantially constant such output of said detector means as the intensity of said light input varies, said feedback means having a relatively slow time constant,
   comparator means for producing a comparison output, said comparator means including means for comparing such output with respect to a threshold signal and for producing said comparison output representative of the result of such comparison, and
   tracking means for causing the value of such threshold signal to track the value of such output relatively slowly, whereby relatively rapid transitions in such output of at least a prescribed magnitude will cause one comparison output and relatively slow variations in such output will result in a different comparison output.

2. The detector system of claim 1, said comparator means including an operational amplifier.

3. The detector system of claim 1, further comprising reference voltage circuit means for producing a reference voltage as such another signal.

4. The detector system of claim 1, said comparator means having at least two inputs for respectively receiving such output and such threshold signal, and said tracking means comprising a resistor capacitor circuit connected to the input receiving such output and to such input receiving such threshold signal.

5. The detector system of claim 1, said detector means comprising a phototransistor, and said feedback means comprising another resistor capacitor circuit for following the output of said phototransistor and a feedback transistor coupled to provide a feedback signal to bias said phototransistor.

6. The detector system of claim 1 further comprising a variable transmission lens, a power supply circuit for operating said lens in at least two different light transmission modes, one being relatively more transmissive and the other being relatively less transmissive, and said power supply circuit being responsive to the cooperative operation of said detector means, feedback means, comparator means, and tracking means to determine the transmissive characteristic of the lens.

7. The detector system of claim 6, said lens comprising a liquid crystal shutter.

8. The detector system of claim 1, further comprising output means for producing an output signal that has a characteristic which is a function of the cooperative operation of said detector means, feedback means, comparator means, and tracking means.

9. The detector system of preceding claim 8, said output means comprising a variable voltage output circuit.

10. The detector system of claim 9, said output means further comprising frequency means for varying the frequency of the output voltage as a function of the cooperative operation of said detector means, feedback means, comparator means and tracking means.

11. The detector system of claim 9, said output means comprising a variable frequency output circuit to produce an output voltage that has at least two diff frequency characteristics as a function of operation of said detector means.

12. A shutter system for controlling transmission of at least one of visible, infrared, and ultraviolet light, comprising
   a variable transmission device for selectively transmitting light as a function of a drive signal thereto,
   output circuit means for delivering such drive signal to said variable transmission device, and
   a detector system for detecting the occurrence of light and controlling operation of said output circuit means, said detector system comprising detector means for receiving a light input and producing an output representative thereof,
   feedback means coupled with respect to said detector means for tending to maintain substantially constant such output of said detector means as the intensity of incident light varies, said feedback means having a relatively slow time constant,
   comparator means for producing a comparison output, said comparator means including
   means for comparing such output with respect to another signal and for producing a comparison output representative of the result of such comparison, and tracking means for causing the value of such another signal to track the value of such output relatively slowly, whereby relatively rapid transitions in such output of at least a prescribed magnitude will cause one comparison output and relatively slow variations in such output will result in a different comparison output.

13. An eye protection system comprising:

detector means for receiving a light input and producing an output representative thereof;

comparator means for producing a comparison output, said comparator means including means for comparing said output with respect to a threshold signal and for producing said comparison output representative of the result of such comparison;

threshold signal developing means for developing said threshold signal, the magnitude of said threshold signal tending to follow the magnitude of said output; and light shutter means for controlling transmission of incident light as a function of said comparison output.

14. The eye protection system of claim 13, wherein the magnitude of said threshold signal tends to remain greater than the magnitude of said output signal.

15. The eye protection system of claim 14, wherein said threshold signal tends to follow the average magnitude of said output.

* * * * *